(12) United States Patent
Yagi et al.

(10) Patent No.: US 8,425,941 B2
(45) Date of Patent: Apr. 23, 2013

(54) POWDER COSMETIC COMPOSITION

(75) Inventors: Katsuhiko Yagi, Yokohama (JP); Sachiko Shirao, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 824 days.

(21) Appl. No.: 12/308,404

(22) PCT Filed: Jul. 25, 2006

(86) PCT No.: PCT/JP2006/315093
§ 371 (c)(1),
(2), (4) Date: Dec. 15, 2008

(87) PCT Pub. No.: WO2008/012922
PCT Pub. Date: Jan. 31, 2008

(65) Prior Publication Data
US 2010/0239680 A1     Sep. 23, 2010

(51) Int. Cl.
*A61K 8/895*     (2006.01)
(52) U.S. Cl.
USPC ............... 424/501; 424/401; 424/63
(58) Field of Classification Search .......... None
See application file for complete search history.

(56) References Cited

U.S. PATENT DOCUMENTS

2004/0096470 A1* 5/2004 Tanaka et al. ............ 424/401
2006/0093565 A1* 5/2006 China et al. .............. 424/63

FOREIGN PATENT DOCUMENTS

| EP | 1 860 137 A1 | 11/2007 |
|---|---|---|
| JP | 6-1709 A | 1/1994 |
| JP | 7-277924 A | 10/1995 |
| JP | 10-36219 A | 2/1998 |
| JP | 2003-81769 A | 3/2003 |
| JP | 2003-81770 A | 3/2003 |
| JP | 3442698 B2 | 9/2003 |
| JP | 2003-292415 A | 10/2003 |
| JP | 2004-217621 A | 8/2004 |
| JP | 2004-231609 A | 8/2004 |

OTHER PUBLICATIONS

Dow Corning 9506 Powder Product Information Personal Care (Mar. 2009).*
Kamei et al., "Development of silicones with surface treatment by powders," Fragrance Journal, Jun. 2002, 81-85, with English abstract.
Product Brochure, "KSP Series, KSP-100.101-105-300, Hybrid silicone powders for personal care," Internet citation, Nov. 2000, 1-7, XP002593966, retrieved from http://www.shinetsusilicones.com/files/KSP.pdf on Jul. 27, 2010.

* cited by examiner

*Primary Examiner* — James H. Alstrum-Acevedo
*Assistant Examiner* — Jessica Kassa
(74) *Attorney, Agent, or Firm* — Foley & Lardner LLP

(57) ABSTRACT

A powder cosmetic composition having satisfactory usability, cosmetic durability, adhesion properties to the skin, slip properties and smoothness comprising, as powder components (a) and (b):
(a) a branched alkyl silicone-treated powder and
(b) a composite silicone elastomer powder coated on all or part of the powder surface with at least one coating selected from the group consisting of clay minerals, resins, metal oxides and salts, in particular including 3 to 80 mass % of the component (a) and 1 to 30 mass % of the component (b).

7 Claims, 1 Drawing Sheet

POWDER COSMETIC COMPOSITION

CROSS-REFERENCE TO RELATED APPLICATIONS

This application is a National Stage application of PCT/JP2006/315093, filed Jul. 25, 2006.

TECHNICAL FIELD

The present invention relates to a powder cosmetic composition, more specifically relates to a powder cosmetic composition used in combination with a specific powder.

The methods for molding powder makeup products such as foundations, eye shadows, rouges, etc. may be largely classified into a dry molding method and a wet molding method. As the former, the compression molding method for compressing the cosmetic base by a press to obtain a predetermined shape is the general method. The latter is the molding method for mixing the cosmetic base with a solvent, filling it into a container, then removing the solvent. In recent years, this has been used in increasing cases in view of the solid feeling and the freedom of multicolor pressing etc. Various methods for producing have been proposed differing in the type of the solvent or the method of removal of the same (see, for example, Japanese Patent Publication (A) No. 7-277924). In powder cosmetic compositions, the feeling in use at the time of application, the beauty of the finish, etc. are carefully evaluated, while the adhesion properties to the skin are not evaluated much at all in practice.

In recent years, for the purpose of improving the usability of foundations, etc., silicone elastomers such as Trefil E-506C (made by Toray Dow Corning) are being used. Such silicone elastomers have distinctive feelings in the use derived from the rubbery elasticity and not seen in other powders such as softness and smoothness. The effects on the improvement of the feeling in use of various types of powder cosmetic compositions is high.

However, such silicone elastomers have a high aggregation ability, and, therefore, in powder cosmetic compositions, with the ordinary dry molding method, cracks and fractures due to poor dispersion of powder easily occur, and, therefore, the amount is limited to about 1 mass %. To solve this problem, from the viewpoint of the production method, the method of using a medium agitation mill or other high dispersion apparatus to break up clumps of silicone elastomer in the solvent to close to the primary particles and wet molding the resultant mixture has been proposed (e.g., see, for example, Japanese Patent Publication (A) No. 2003-81769). Further from the viewpoint of the materials, at the time of synthesis of a silicone elastomer, a composite silicone elastomer comprised of an elastomer on the surface of which a silicone resin is partially coated (KSP Series made by Shin-Etsu Chemical Co., Ltd.) and a composite silicone elastomer obtained by mechanically crushing clumps of a silicone elastomer to the primary particles and mechanochemically coating an inorganic compound such as a clay mineral on the surface of the silicone elastomer (e.g., see, for example, Japanese Patent No. 3442698) have been proposed.

Regarding this composite silicone elastomer, not only the effects in production and feeling of suppressing the aggregation of powder, but also other functions can be given to the elastomer per se. When coating a substance having an ultraviolet shielding effect, such as titanium oxide not only a good feeling, but also an ultraviolet protection capability and also, in the case of iron oxide, a hue correction effect can be imparted.

In particular, by combining a plurality of coatings, it is possible to give completely new value to the elastomer per se. A composite silicone elastomer comprised of a silicone resin-coated silicone elastomer powder coated with particulate zinc oxide on the surface thereof by a mechanochemical method is known to be not only superior in the feeling when applied, but also to inhibit the activity of the plasminogen activating enzyme urokinase present on the skin surface and causing skin roughness to thereby alleviate skin roughness (see Japanese Patent Publication (A) No. 2004-217621).

DISCLOSURE OF THE INVENTION

However, the powder cosmetic composition containing this powder has low adhesion property to the skin and easily results in ruined cosmetic finish. The slip is good, but the smoothness is insufficient. Further, when makeup products are produced by compression molding, if a large amount of smooth powder with good slip is formulated, the cohesion becomes too great, the pickup by a coating applicator such as a sponge is decreased, that is a so-called caking phenomenon occurs, and conversely the compression becomes insufficient and problems in physical properties such as insufficient composition and decrease in the drop strength occur.

An object of the present invention is to solve the above conventional problems and to provide a powder cosmetic composition having a satisfactory usability, cosmetic durability, and adhesion property to the skin.

The inventors engages in intensive research to solve the above problems and, as a result, discovered that, by using a composite silicone elastomer powder coated on all or part of the powder surface with at least one coating selected from clay minerals, resins, metal oxides and salts, in combination with a branched alkyl silicone-treated powder, it is possible to obtain a powder cosmetic composition having a good usability, preventing ruined makeup and superior in adhesion property to the skin, whereby the present invention have been completed.

The present invention is a powder cosmetic composition comprising, as powder components (a) and (b), (a) a branched alkyl silicone-treated powder and (b) a composite silicone elastomer powder coated on all or part of the powder surface with at least one coating selected from the group consisting of clay minerals, resins, metal oxides and salts.

In the present invention, preferably the amount of the component (a) is 3 to 80 mass % and the amount of the component (b) is 1 to 30 mass %.

In the present invention, preferably the component (b) is a composite silicone elastomer powder having a coating of 1 to 300 parts by mass, based upon 100 parts by mass of a silicone elastomer powder.

In the present invention, the above powder cosmetic composition is a foundation or eye shadow.

According to the present invention, a powder cosmetic composition having a satisfactory usability, cosmetic durability, adhesion property to the skin, excellent slip and smoothness can be obtained.

BEST MODE FOR CARRYING OUT THE INVENTION

Figure 1:
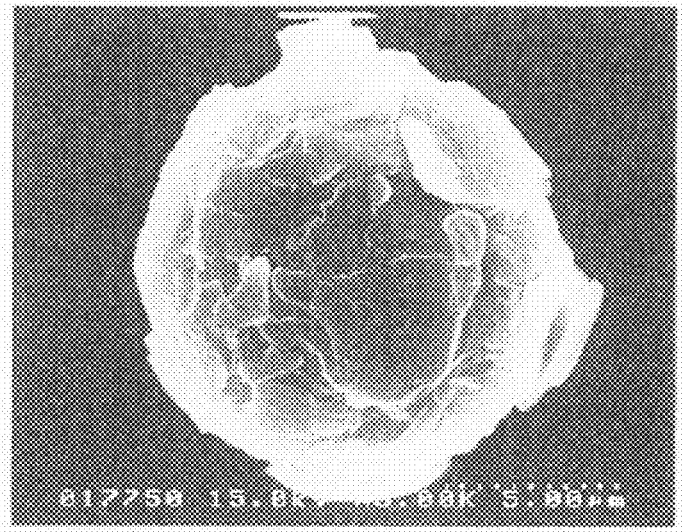
FIG. 1 is a SEM photograph of the powder surface of the composite silicone elastomer produced in Production Example 1.

The best mode for carrying out the present invention will be explained below.

Branched Alkyl Silicone-Treated Powder

The branched alkyl silicone-treated powder usable in the present invention can be obtained by adding a branched alkyl silicone treatment agent, for example, KF-9909 made by Shin-Etsu Chemical Co., Ltd. expressed by the following general formula (I), and a mixed solvent of a volatile organic solvent such as isopropyl alcohol to a powder, uniformly stirring the mixture by a mixer such as a Henschel mixer, and removing the solvent at a heating step.

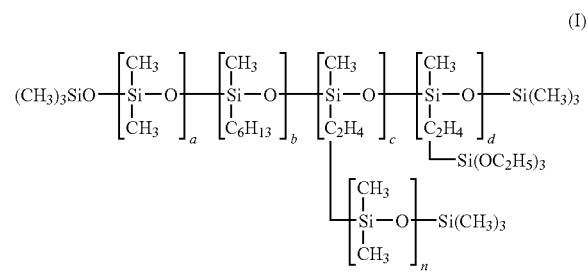

wherein a=5 to 15, b=1 to 5, c=1 to 3, d=1 to 5, and n=3 to 15.

As the powder usable here, body pigments and coloring materials may be mentioned. For example, talc, mica, sericite, kaolin, synthetic mica, calcium carbonate, magnesium carbonate, silica, aluminum oxide, barium sulfate, boronitride, acryl-based polymer, nylon, polystyrene, polyethylene, polypropylene, polyurethane, cellulose, silicone or their copolymers and other spherical resin powders, inorganic coloring materials, etc. may be mentioned. Among these, in particular, one or more of pigments selected from mica, sericite, talc, kaolin, synthetic mica, iron oxide and titanium oxide are preferably used.

Further, it is also possible to use a commercially available branched alkyl silicone-treated powder. Such a branched alkyl silicone-treated powder, includes, for example, NS Talc JA-46R-3S, NS Sericite FSE-3S, NS Eightpearl 300S-2S, NS Eightpearl 1000S-2S, NS Mica Y-3000-3S (above made by Kakuhachi Co., Ltd.), BAE-Talc JA-68R, BAE-Sericite FSE, BAE-Mica M-102, BAE-Titanium CR-50, BAE-Yellow-LLXLO, BAE-Bengara Shippo, BAE-Black BL 100 (above made by Miyoshi Kasei Industry), etc.

The particularly preferable branched alkyl silicone-treated powder is a powder of KF-9909 made by Shin-Etsu Chemical Co., Ltd., a modified silicone comprised of a silicone main chain having a silicone side chain and alkyl side chain and having an ethoxy group(s) as the reaction site with powder, treated by make it hydrophobic. This branched alkyl silicone-treated powder is extremely strong in the hydrophobicity and water-proofness and is extremely superior in adhesion property onto the skin.

In the present invention, the content of the branched alkyl silicone-treated powder of 3 to 80 mass % in the total powder cosmetic composition is preferable from the viewpoint of imparting a smooth moist feeling in use and improving the adhesion property to the skin. 5 to 50 mass % is more preferable.

Composite Silicone Elastomer Powder

As the composite silicone elastomer powder usable in the present invention, there are mica-coated silicone elastomer powder, sericite-coated silicone elastomer powder, talc-coated silicone elastomer powder, kaolin-coated silicone elastomer powder, boronitride-coated silicone elastomer powder, silicone resin-coated silicone elastomer powder, silicone resin-coated phenyl rubber powder, silica-coated silicone elastomer powder, titanium oxide-coated silicone elastomer powder, zinc oxide-coated silicone elastomer powder, cerium oxide-coated silicone elastomer powder, iron oxide-coated silicone elastomer powder, silica/silicone resin-coated silicone elastomer powder, titanium oxide/silicone resin-coated silicone elastomer powder, zinc oxide/silicone resin-coated silicone elastomer powder, cerium oxide/silicone resin-coated silicone elastomer powder, titanium oxide/silicone resin-coated phenyl rubber powder, zinc oxide/silicone resin-coated phenyl rubber powder, cerium oxide/silicone resin-coated phenyl rubber powder, iron oxide/silicone resin-coated silicone elastomer powder, etc.

Among these, in particular, composite silicone elastomer powders comprised of the Trefil E Series made by Toray Dow Corning (Trefil E-505C, Trefil E-506S, Trefil E-507, and Trefil E-508) coated on the surface thereof with talc, sericite, kaolin, mica, titanium mica, or another clay mineral are preferable.

Further, as commercially available products of composite silicone elastomer powder, for example, the silicone resin-coated silicone elastomers KSP-100, KSP-101, KSP-102, and KSP-105 (made by Shin-Etsu Chemical Co., Ltd.) and the silicone resin-coated phenyl rubber powder KSP-300 (made by Shin-Etsu Chemical Co., Ltd.) etc. may be mentioned.

The coating amount of the composite silicone elastomer powder used in the present invention is preferably 1 to 300 parts by mass, based upon 100 parts by mass of the core silicone elastomer powder, more preferably 3 to 250 parts by mass. If the coating amount is smaller than 1 part by mass, agglomeration of the silicone elastomer powder itself cannot be suppressed and the dispersability of the powder is remarkably decreased, and, therefore, the formulating amount into cosmetic compositions is limited and the targeted feeling in use or cosmetic durability cannot be achieved. If the amount is larger than 300 parts by mass, the feeling in use of the coating is too strongly brought out, and therefore, so the soft feeling in use distinctive to silicone elastomers tends to disappear. Further, the coating may be a single layer or multiple layers. For example, the Production Examples 4 to 6 explained below correspond to multiple layers.

The content of the composite silicone elastomer powder usable in the present invention is preferably 1 to 30 mass %, more preferably 3 to 20 mass % in the total cosmetic composition. If the content of the composite silicone elastomer powder is smaller than 1 mass %, the ease of application and the slip are decreased and a caking phenomenon is sometime caused. If the content is more than 30 mass %, cracks and fractures easily occur and problems arise in production.

Others

The powders other than the above essential ingredients usable in the present invention, other than coloring agents, are not particularly limited so long as powders can be formulated into cosmetic compositions. The examples of the powders, while there is some overlap with the above, include talc, mica, sericite, kaolin, synthetic mica, calcium carbonate, magnesium carbonate, silica, aluminum oxide, barium sulfate, boronitride, acryl-based polymers, nylon, polystyrene, polyethylene, polypropylene, polyurethane, cellulose, silicone, or their copolymers and other spherical resin powders etc. may be mentioned. The powder in the present invention may be one or two or more types freely selected and formulated.

In the present invention, when these powders are hydrophilic, it is possible to use them after treatment to make them hydrophobic. The treatment method for making them hydrophobic is not particularly limited. For example, the treatment method with silicone, by fluorine, a coupling agent, a metal soap, a fatty acid, a surfactant, or an acid, alkali, and inorganic salt and further composite treatment thereof, etc. may be used.

In the present invention, it is possible to formulate a coloring agent. As specific examples of coloring agents, titanium oxide, zinc oxide and other inorganic white pigments, yellow iron oxide, bengara, black iron oxide, and other inorganic coloring pigments, titanium mica, iron oxide titanium mica, titanium oxide-coated synthetic mica and other pearl agents, tar colors and other organic coloring agents, etc. may be mentioned.

In the present invention, an oil agent is preferably formulated. The oil agent is not particularly limited if an oil agent used as an oil agent for cosmetic compositions in the past. An ester, hydrocarbon, higher fatty acid, higher alcohol, silicone oil, etc. may be mentioned. Examples of the oil agent includes an ester, for example, olive oil, castor oil, jojoba oil, macadamia nut oil, or other lipids, isopropyl myristate, isopropyl palmitate, cetyl 2-ethylhexanoate, octyl dodecyl myristate, and other fatty acid monoesters, glyceryl trioctanoate, glyceryl triisostearate, and other glyceryl esters, diglyceryl diisostearate, diglyceryl triisostearate, and other polyglyceryl esters, pentaerythritol di-2-ethyl hexanoate, pentaerythritol dioctanoate, or other pentaerythritol ester, trimethylol propane trioctanoate, trimethylol propane triisostearate, and other trimethylol propane esters, isostearyl malate, and other malic acid esters etc. Further, as hydrocarbons, for example, liquid paraffin, squalene, polybutene, liquid lanolin, volatile hydrocarbon, etc. may be mentioned. Further, as higher fatty acids, for example, isostearic acid, oleic acid, etc. may be mentioned. Further, as the higher alcohols, for example, isostearyl alcohol, oleyl alcohol, octyl dodecanol, etc. may be mentioned. Further, as the silicone oils, for example, dimethyl polysiloxane, methylphenyl polysiloxane, diphenyl polysiloxane, cyclic silicone (octamethyl cyclotetrasiloxane, decamethyl cyclopentasiloxane, dodecamethyl cyclohexane siloxane, etc.), amino-modified polysiloxane, alkyl-modified polysiloxane, fluorine-modified polysiloxane, etc. may be mentioned.

Among the above optional ingredients, the solid oils are not particularly limited so long as oils which can be formulated into cosmetic compositions. Examples of solid oils, for example, solid paraffin, ceresin, microcrystalline wax, polyethylene wax, hardened oil, beeswax, Japan wax, spermaceti wax, candellila wax, and other hydrocarbons, waxes, and stearic acid, lauric acid, myristic acid, behenic acid, and other higher fatty acids, cetyl alcohol, stearyl alcohol, lauryl alcohol, and other higher alcohols, etc. may be mentioned.

The powder cosmetic composition of the present invention may have suitably formulated thereinto, in addition to the above ingredients, other ingredients usually used in cosmetic compositions, quasi-drugs, pharmaceuticals, etc. within a range not detracting from the effect of the present invention. As other ingredients, for example, a surfactant, humectant, polymer, dye, lower alcohol, polyhydric alcohol, antioxidant, UV absorber, beauty ingredient, antibacterial agent, preservative, pH adjuster, fragrance, etc. may be mentioned.

The production method of the powder cosmetic composition of the present invention is not particularly limited and can be produced by the dry press molding method, the wet molding method, etc. In the present invention, due to the superiority of the dispersability of the powder, production by the usual dry press molding is preferable from the viewpoint of the cost and production.

In the case of the wet molding method, as the usable solvent, ethanol, isopropyl alcohol, water, hexane, volatile silicone, light isoparaffin, etc. may be mentioned. In particular, ethanol is preferable. The amounts are not particularly limited, since they are determined by the formulation of the cosmetic base and the fillability inside the dish, but usually 10 to 100 parts by mass, based upon 100 parts by mass of the cosmetic base is suitable. In particular, in the case of ethanol, 20 to 70 parts by mass are preferable.

As the powder cosmetic composition of the present invention, a foundation, makeup base, whitening powder, rouge, etc. may be mentioned, but the cosmetic compositions where the effect of present invention is remarkably exhibited are foundations and eye shadow.

EXAMPLES

Examples will now be used to explain in further detail the present invention. Note that the present invention is not limited by these Examples. The amounts of the ingredients in the Examples of the cosmetic compositions are shown by mass % based upon the total amounts of the cosmetic compositions.

In Production Examples 1 to 5, composite silicone elastomer powders of the ingredient (b) used in the present invention were produced under various types of conditions.

Production Example 1

Production of Composite Silicone Elastomer Powder

As the silicone elastomer powder, 40 parts of Trefil E-506S made by Toray Dow Corning were used, while as the clay mineral, 60 parts of talc (JA-68R made by Asada Milling Co., Ltd., average particle size 9.0 to 12.0 μm) were used.

These materials were charged into a high speed rotary disperser. Cooling water was flowed through the jacket part of the disperser and the disperser was rotated at a low speed of a peripheral speed of 20 m/s for 3 minutes to mix the treated materials. Next, the materials were treated at a peripheral speed of 40 m/s at a high speed rotation of Froude number of 70 or more for 60 minutes. The temperature of the treated powder rapidly increased and became constant at 40 to 60° C. after 2 to 3 minutes. After 60 minutes, the high speed rotation was stopped, the disperser was rotated at a peripheral speed of 20 m/s or less, then the composite compound was cooled to room temperature and recovered to obtain a talc-coated silicone elastomer.

Production Examples 2 and 3

Production of Composite Silicone Elastomer Powder

The method described in Production Example 1 was used to obtain a mica/resin-coated silicone elastomer (Production Example 2) and a boronitride-coated silicone elastomer (Production Example 3).

Production Example 4

Production of Composite Silicone Elastomer Powder

To 83 parts of a silicone resin-coated silicone elastomer (KSP-100 made by Shin-Etsu Chemical Co., Ltd.), 17 parts of particulate zinc oxide (zinc white (Seido)) were added. A Henschel mixer was used for prestirring, then 3 mmφ aluminum balls were used to form a composite in a ball mill. A sieving step was used for removal of the coarse particle part to obtain a zinc oxide/silicone resin-coated silicone elastomer.

Production Example 5 and 6

Production of Composite Silicone Elastomer Powder

The method described in Production Example 4 was used to obtain a titanium oxide/silicone resin-coated silicone elastomer (Production Example 5) and an iron oxide/silicone resin-coated silicone elastomer (Production Example 6).

Figure 2:
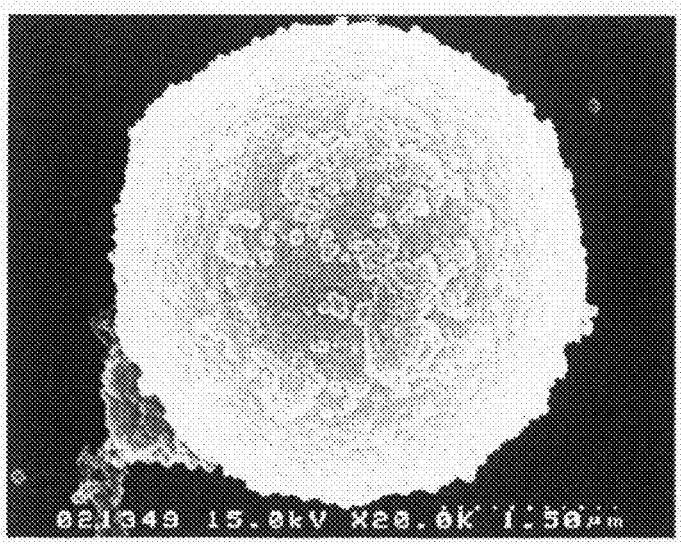
FIG. 2 is a SEM photograph of the powder surface of a commercially available composite silicone elastomer.

SEM photos of the powder surfaces of the composite silicone elastomer powder obtained in Production Example 1 and a commercially available silicone resin-coated phenyl rubber powder (KSP-300 made by Shin-Etsu Chemical Co., Ltd.) are shown in FIGS. 1 and 2. From FIG. 1, the powder of Production Example 1 was a composite silicone elastomer uniformly coated on the entire surface of the silicone elastomer with talc. Further, from FIG. 2, the commercially available composite silicone elastomer was structured partially covered by a silicone resin. Both of these were used as the component (b) of the present invention.

In this way, the various types of composite silicone elastomer powders used in the present invention were coated with a coating on all or part of the surface of the silicone elastomer.

The various types of cosmetic compositions containing the composite silicone elastomer powders of the above Production Examples were tested for use by a panel of 20 experts and evaluated for pickup of the cosmetic composition by the applicator, ease of application of the cosmetic composition at the time of application, adhesion properties to the applied location, smoothness of the skin after the application, and other feelings in use and usability, based on the following criteria for evaluation. Next, the averages of the scores given by the panelists were used to evaluate the properties in use.

Criteria for Evaluation
5 points: extremely superior
4 points: superior
3 points: usual
2 points: poor
1 point: extremely poor Example 1 and Comparative Examples 1 to 3

Powdery foundations were produced by the dry method according to the formulations of Table I and were evaluated for smoothness, moistness, fit to skin, lack of powderiness and lack of ruined makeup in according to the above criteria. The results are shown together in Table I.

TABLE I

| | Ex. 1 | Comp. Ex. 1 | Comp. Ex. 2 | Comp. Ex. 3 |
|---|---|---|---|---|
| Branched alkyl silicone-coated talc (*1) | Bal. | — | — | Bal. |
| Branched alkyl silicone-coated sericite (*2) | 15 | — | — | 15 |
| Branched alkyl silicone-coated mica (*3) | 10 | — | — | 10 |
| Talc | — | Bal. | Bal. | — |
| Sericite | — | 15 | 15 | — |
| Mica | — | 10 | 10 | — |
| Silicone-treated titanium oxide (*4) | 10 | 10 | 10 | 10 |
| Bengara | 0.8 | 0.8 | 0.8 | 0.8 |
| Yellow iron oxide | 2 | 2 | 2 | 2 |
| Black iron oxide | 0.1 | 0.1 | 0.1 | 0.1 |
| Talc-coated silicone elastomer (Production Example 1) | 10 | — | 10 | — |
| Spherical polyacrylic acid alkyl powder | — | 5 | — | 5 |
| Spherical silica | — | 5 | — | 5 |
| Fine particle zinc oxide | 1 | 1 | 1 | 1 |
| Fine particle titanium oxide | 3 | 3 | 3 | 3 |
| Synthetic phlogopite | 1 | 1 | 1 | 1 |
| Bengara-coated titanium mica | 1 | 1 | 1 | 1 |
| 2-ethylhexy p-methoxycinnimate | 3 | 3 | 3 | 3 |
| Dimethyl polysiloxane | 5 | 5 | 5 | 5 |
| Isostearyl malate | 1 | 1 | 1 | 1 |
| Glyceryl tri-2-ethylhexanoate | 3 | 3 | 3 | 3 |
| Sorbitan sesquiisostearate | 1 | 1 | 1 | 1 |
| Ethyl paraben | q.s. | q.s. | q.s. | q.s. |
| Antioxidant | q.s. | q.s. | q.s. | q.s. |
| Fragrance | q.s. | q.s. | q.s. | q.s. |
| Smoothness | 4.85 | 1.25 | 3.55 | 1.40 |
| Moistness | 4.75 | 1.20 | 3.20 | 1.35 |
| Fit to skin | 4.90 | 1.25 | 1.10 | 3.20 |
| Lack of powderiness | 4.80 | 1.15 | 1.15 | 3.40 |
| Lack of ruined makeup | 4.80 | 1.10 | 2.10 | 2.50 |

(*1) BAE-Talc JA68R (made by Miyoshi Kasei Industry)
(*2) BAE-Sericite FSE (made by Miyoshi Kasei Industry)
(*3) BAE-mica M-102 (made by Miyoshi Kasei Industry)
(*4) Titanium Oxide MT020 (made by Tayca Corporation)

The production methods of the Examples and Comparative Examples were, based on the production method of usual powder solid cosmetic compositions. That is, the powder part including the branched alkyl silicone-coated powder and composite silicone elastomer is stirred using a Henschel mixer. Thereafter, the oil component is added and the resultant mixture further stirred, then if necessary crushed. Further, the steps of adding and agitating the pearl agent and other components which might be damaged in feeling of quality due to crushing after the crushing, etc. are possible.

As is clear from the results of Table I, the foundation of Example 1 containing the branched alkyl silicone-coated powder and composite silicone elastomer powder was superior in the cosmetic durability, lack of powderiness, and fit to the skin, that is, good adhesion, in finish. Furthermore, in terms of feeling in use as well, it had a smooth and moist feeling.

As opposed to this, the foundation of Comparative Example 1 not containing either the branched alkyl silicone-coated powder or composite silicone elastomer powder was powdery, was poor in fit to the skin and did not have a good cosmetic durability in finish. Further, the foundations of Comparative Examples 2 to 3 containing either the branched alkyl silicone-coated powder or the composite silicone elastomer powder lacked powderiness and had a good adhesion with a feeling of fit to the skin in finish when containing only the branched alkyl silicone-coated powder, but lacked smoothness and was poor in cosmetic durability. Further, when containing only the composite silicone elastomer powder, it was powdery, lacked a feeling of fit to the skin and lacked adhesion in finish.

Example 2 and Comparative Examples 4 and 5

Powdery foundations were made by the wet method with the formulations of Table II and were evaluated by the above criteria for smoothness, moistness, fit to skin, lack of powderiness, and lack of ruined makeup. The results are shown in Table II.

TABLE II

|  | Ex. 2 | Comp. Ex. 4 | Comp. Ex. 5 |
|---|---|---|---|
| Branched alkyl silicone-coated talc (*1) | Bal. | — | — |
| Branched alkyl silicone-coated sericite (*2) | 15 | — | — |
| Branched alkyl silicone-coated mica (*3) | 10 | — | — |
| Dimethyl silicone-coated talc (*5) | — | Bal. | — |
| Dimethyl silicone-coated sericite (*6) | — | 15 | — |
| Dimethyl silicone-coated mica (*7) | — | 10 | — |
| Acryl silicone-coated talc (*8) | — | — | Bal. |
| Acryl silicone-coated sericite (*9) | — | — | 15 |
| Acryl silicone-coated mica (*10) | — | — | 10 |
| Silicone-treated titanium oxide (*4) | 10 | 10 | 10 |
| Bengara | 0.8 | 0.8 | 0.8 |
| Yellow iron oxide | 2 | 2 | 2 |
| Black iron oxide | 0.1 | 0.1 | 0.1 |
| Talc-coated silicone elastomer (Production Example 1) | 10 | 10 | 10 |
| Fine particle zinc oxide | 1 | 1 | 1 |
| Fine particle titanium oxide | 3 | 3 | 3 |
| Synthetic phlogopite | 1 | 1 | 1 |
| Bengara-coated titanium mica | 1 | 1 | 1 |
| 2-ethylhexyl p-methoxycinnimate | 3 | 3 | 3 |
| Dimethyl polysiloxane | 5 | 5 | 5 |
| Isostearyl malate | 1 | 1 | 1 |
| Glyceryl tri-2-ethylhexanoate | 3 | 3 | 3 |
| Sorbitan sesquiisostearate | 1 | 1 | 1 |
| Ethyl paraben | q.s. | q.s. | q.s. |
| Antioxidant | q.s. | q.s. | q.s. |
| Fragrance | q.s. | q.s. | q.s. |
| Smoothness | 4.85 | 4.00 | 3.85 |
| Moistness | 4.75 | 4.00 | 3.80 |
| Fit to skin | 4.90 | 3.75 | 3.20 |
| Lack of powderiness | 4.80 | 4.15 | 4.25 |
| Lack of ruined makeup | 4.80 | 4.10 | 4.10 |

(*5) SA-talc JA68R (made by Miyoshi Kasei Industry)
(*6) SA-sericite FSE (made by Miyoshi Kasei Industry)
(*7) SA-micaM-102 (made by Miyoshi Kasei Industry)
(*8) ASE-talc JA68R (made by Miyoshi Kasei Industry)
(*9) ASE-sericite FSE (made by Miyoshi Kasei Industry)
(*10) ASE-micaM-102 (made by Miyoshi Kasei Industry)

The production methods of the Examples and Comparative Examples were based on the production method of usual powder solid cosmetic compositions. That is, the powder part including the branched alkyl silicone-coated powder and composite silicone elastomer is stirred using a Henschel mixer. Thereafter, the oil component is added and the resultant mixture further stirred, then if necessary crushed. Further, the steps of adding and agitating the pearl agent and other components which might be damaged in feeling of quality due to crushing after the crushing etc. are possible.

As is clear from the results of Table II, the foundation of Example 2 containing the branched alkyl silicone-coated powder and composite silicone elastomer powder was superior in cosmetic durability, lack of powderiness and fit to the skin, that is, good adhesion, in finish. Furthermore, in terms of feeling in use as well, it had a smooth and moist feeling.

As opposed to this, the foundations of Comparative Examples 4 to 5 containing dimethyl silicone-coated powder or acryl silicone-coated powder and composite silicone elastomer powder lacked smoothness, moistness, and fit to skin compared with Example 2. In particular, compared with Example 2, a large difference in fit to skin was seen.

Examples 3 to 5 and Comparative Example 6

Powdery foundations were produced by the dry method according to the formulations of Table III and were evaluated for smoothness, moistness, fit to skin, lack of powderiness, and lack of ruined makeup in according to the above criteria. The results are shown together in Table III.

TABLE III

|  | Ex. 3 | Ex. 4 | Ex. 5 | Comp. Ex. 6 |
|---|---|---|---|---|
| Branched alkyl silicone-coated talc (*1) | Bal. | Bal. | Bal. | Bal. |
| Branched alkyl silicone-coated sericite (*2) | 15 | 15 | 15 | 15 |
| Branched alkyl silicone-coated mica (*3) | 10 | 10 | 10 | 10 |
| Silicone-treated titanium oxide | 10 | 10 | 10 | 10 |
| Bengara | 0.8 | 0.8 | 0.8 | 0.8 |
| Yellow iron oxide | 2 | 2 | 2 | 2 |
| Black iron oxide | 0.1 | 0.1 | 0.1 | 0.1 |
| Silicone resin-coated silicone elastomer powder (*11) | 10 | — | 30 | — |
| Silicone resin-coated phenyl rubber powder (*12) | — | 10 | — | — |
| Silicone elastomer (*13) | — | — | — | 10 |
| Zinc oxide-silicone resin coating |  |  |  |  |
| Silicone elastomer powder (Production Example 4) | 1 | 1 | 1 | 1 |
| Fine particle titanium oxide | 3 | 3 | 3 | 3 |
| Synthetic phlogopite | 1 | 1 | 1 | 1 |
| Bengara-coated titanium mica | 1 | 1 | 1 | 1 |
| 2-ethylhexyl p-methoxycinnimate | 3 | 3 | 3 | 3 |
| Dimethyl polysiloxane | 5 | 5 | 5 | 5 |
| Isostearyl malate | 1 | 1 | 1 | 1 |
| Glyceryl tri-2-ethylhexanoate | 3 | 3 | 3 | 3 |
| Sorbitan sesquiisostearate | 1 | 1 | 1 | 1 |
| Ethyl paraben | q.s. | q.s. | q.s. | q.s. |
| Antioxidant | q.s. | q.s. | q.s. | q.s. |
| Fragrance | q.s. | q.s. | q.s. | q.s. |
| Smoothness | 4.80 | 4.90 | 4.15 | 1.40 |
| Moistness | 4.75 | 4.85 | 4.10 | 1.30 |
| Fit to skin | 4.70 | 4.90 | 4.20 | 1.20 |
| Lack of powderiness | 4.80 | 4.90 | 4.20 | 1.25 |
| Lack of ruined makeup | 4.75 | 4.80 | 4.70 | 2.60 |
| Drop strength (times) (*14) | 15.3 | 14.6 | 14.3 | 2 |

(*11) KSP-100 (made by Shin-Etsu Chemical Co., Ltd.)
(*12) KSP-300 (made by Shin-Etsu Chemical Co., Ltd.)
(*13) Trefil E-506S (made by Toray Dow Corning Silicone)
(*14) Drop strength: A sample was dropped on an iron plate from a height of 30 cm. The number of times until half the amount is lost is counted (N = 3).

The production methods of the Examples and Comparative Examples were based on the production method of usual powder solid cosmetic compositions. As an example, the powder part including the branched alkyl silicone-coated powder and composite silicone elastomer is stirred using a Henschel mixer. Thereafter, the oil component is added and the resultant mixture further stirred, then if necessary, crushed. Further, the steps of adding and agitating the pearl agent and other components which might be damaged in feeling of quality due to crushing after the crushing etc. are possible.

As is clear from the results of Table III, the foundations such as in Examples 3 and 4 containing the branched alkyl silicone-coated powder and silicone resin-coated elastomer powder or silicone resin-coated phenyl rubber powder were superior in cosmetic durability, lack of powderiness, and fit to the skin, that is, good adhesion, in finish. Furthermore, in terms of feeling in use as well, they had smooth and moist feelings.

Further, the foundation such as in Example 5 containing the silicone resin-coated silicone elastomer powder in 30 massa, compared with that containing it in 10 mass %, was somewhat inferior in smoothness, moistness, etc., but was sufficiently good in results.

As opposed to this, a foundation like in Comparative Example 6 containing a branched alkyl silicone-coated powder and usual silicone elastomer exhibited a powderiness and lacked smoothness and moistness. Further, sufficient drop strength could not be exhibited.

Example 6 and Comparative Example 7

Eye shadows were produced by the dry method by the formulations of the following Table IV and were evaluated by the above criteria for smoothness, moistness, fit to skin, lack of powderiness, lack of ruined makeup, and drop strength. The results are shown together in Table IV.

TABLE IV

|  | Ex. 6 | Comp. Ex. 7 |
|---|---|---|
| Branched alkyl silicone-treated talc (*1) | Bal. | — |
| Branched alkyl silicone-treated mica (*3) | 10 | — |
| Synthetic phlogopite | 2 | 2 |
| Branched alkyl silicone-treated sericite (*2) | 30 | — |
| Talc | — | Bal. |
| Mica | — | 10 |
| Sericite | — | 30 |
| Titanium oxide | 1 | 1 |
| Zinc myristate | 2 | 2 |
| Talc-coated silicone elastomer (Production Example 1) | 10 | — |
| Silicone elastomer | — | 10 |
| Yellow iron oxide | 2 | 2 |
| Black iron oxide | 5 | 5 |
| Titanium mica | 5 | 5 |
| Color | q.s. | q.s. |
| Diisostearyl malate | 3 | 3 |
| Liquid paraffin | 0.5 | 0.5 |
| Vaseline | 1 | 1 |
| Methylphenyl polysiloxane | 2 | 2 |
| Sorbitan sesquiisostearate | 1 | 1 |
| Antioxidant | q.s. | q.s. |
| P-oxybenzoic acid ester | q.s. | q.s. |
| Smoothness | 4.80 | 1.20 |
| Moistness | 4.75 | 1.30 |
| Fit to skin | 4.70 | 1.15 |
| Lack of powderiness | 4.65 | 1.25 |
| Lack of ruined makeup | 4.80 | 1.15 |
| Drop strength (*14) | 12.6 | 2.3 |

The production method of the eye shadows of the above Example and Comparative Example was based on the production method of ordinary powder solid cosmetic compositions. As an example, the powder components including the branched alkyl silicone-coated powder and composite silicone elastomer are agitated using a Henschel mixer. After that, the oil component is added and the resultant mixture further agitated, then, if necessary, is crushed. Further, the steps of adding and agitating the pearl agent and other components which might be damaged in feeling of quality due to crushing after the crushing etc. are possible.

As is clear from the results of Table IV, the eye shadow containing a branched alkyl silicone-coated powder and composite silicone elastomer (Example 6) was superior in the points of smoothness, moistness, fit to skin, and lack of powderiness compared with Comparative Example 7. Further, there were also good results in the drop strength.

Other formulations being worked will be shown below.

Example 7

Wet Formed Powdery Foundation

| | |
|---|---|
| Branched alkyl silicone-treated sericite | 10 mass % |
| Branched alkyl silicone-treated talc | 5 |
| Branched alkyl silicone-treated mica | Bal. |
| Alkyl-modified silicone resin-treated yellow iron oxide | 2 |
| Alkyl-modified silicone resin-coated bengara | 1 |
| Alkyl-modified silicone resin-coated black iron oxide | q.s. |
| Alkyl-modified silicone resin-coated titanium oxide | 10 |
| Dibasic calcium phosphate | 3 |
| Low temperature fired zinc oxide | 5 |
| Barium sulfate | 2 |
| Mica-coated silicone elastomer (Production Example 2) | 8 |
| 2-ethylhexyl p-methoxycinnimate | 3 |
| Anhydrous silicic acid | 1 |
| Titanium oxide | 2 |
| α-olefin oligomer | 3 |
| Dimethyl polysiloxane | 8 |
| Methyl hydrogen polysiloxane | 0.5 |
| Sorbitan sesquiisostearate | 1 |
| Antioxidant | q.s. |
| Preservative | q.s. |

Example 8

Loose Type White Powder

| | |
|---|---|
| Branched alkyl silicone-coated talc | Bal. |
| Branched alkyl silicone-coated mica | 20 mass % |
| Zinc myristate | 3 |
| Aluminum stearate | 0.1 |
| Anhydrous silicic acid | 5 |
| Boronitride-coated silicone elastomer (Production Example 3) | 30 |
| Anhydrous silicic acid | 6 |
| Bengara-coated titanium mica | 2 |
| Yellow iron oxide | 0.1 |
| Color | q.s. |
| Antioxidant | q.s. |
| Preservative | q.s. |
| Fragrances | q.s. |

Example 9

W/O Emulsion Type Foundation

| | |
|---|---|
| Dimethyl polysiloxane | 15 mass % |
| Decamethyl cyclopentasiloxane | 20 |
| Polyoxyethylene methyl polysiloxane copolymer | 5 |
| High molecular weight amino-modified silicone | 0.1 |
| Glyceryl | 5 |
| 1,3-butylene glycol | 10 |
| Palmitic acid | 0.5 |
| Macadamia nut oil fatty acid cholesterol | 0.1 |
| Distearyl dimethyl ammonium chloride | 0.2 |
| Branched alkyl silicone-coated yellow iron oxide (*15) | 2 |
| Branched alkyl silicone-coated bengara (*16) | 1 |
| Branched alkyl silicone-coated black iron oxide (*17) | 0.3 |
| Branched alkyl silicone-coated titanium oxide (*18) | 7 |
| Branched alkyl silicone-coated talc | 5 |

| | |
|---|---|
| Silicone-coated spindle shaped titanium oxide | 3 |
| Silicone resin-coated silicone elastomer (*11) | 5 |
| Sodium L-glutamate | 0.5 |
| DL-α-tocopherol acetate | q.s. |
| P-oxybenzoic acid ester | q.s. |
| Methyl bistrimethoxycinnimate | q.s. |
| (Trimethylsiloxy)silylisopentyl | 0.1 |
| Dimethyl distearyl ammonium hectorite | 1.5 |
| Talc-coated silicone elastomer (Production Example 1) | 5 |
| Refined water | Bal. |
| Fragrance | q.s. |

(*15) BAE-Yellow-LLXLO(made by Miyoshi Kasei Industry)
(*16) BAE-Bengara Shippo (made by Miyoshi Kasei Industry)
(*17) BAE-Black BL-100 (made by Miyoshi Kasei Industry)
(*18) BAE-Titanium CR-50 (made by Miyoshi Kasei Industry)

Example 10

W/O 2-Layer Dispersion Type Milky Foundation

| | |
|---|---|
| Decamethyl cyclopentasiloxane | 10 mass % |
| Dodecamethyl cyclohexasiloxane | 20 |
| Trimethylsiloxysilicic acid | 1 |
| Poly(oxyethylene oxypropylene)methyl polysiloxane copolymer | 3 |
| Ethanol | 10 |
| Isostearic acid | 0.5 |
| Branched alkyl silicone-coated titanium oxide (*12) | 10 |
| Branched alkyl silicone-coated talc (*1) | 5 |
| Needle-like particle titanium oxide | 1 |
| Spherical anhydrous silicic acid | 5 |
| Titanium oxide-silicone resin-coated silicone elastomer powder (Production Example 5) | 5 |
| Branched alkyl silicone-coated mica | q.s. |
| Sodium citrate | q.s. |
| N-lauroyl-L-lysine | 0.5 |
| DL-α-tocopherol acetate | 0.1 |
| D-δ-tocopherol | 0.1 |
| *Sophora angustifolia* extract | 1 |
| Branched alkyl silicone-coated bengara (*10) | q.s. |
| Branched alkyl silicone-coated yellow iron oxide (*9) | q.s. |
| Branched alkyl silicone-coated black iron oxide (*11) | q.s. |
| *Melilotus officinalis* extract | 2 |
| Refined water | Bal. |

Example 11

Oily Two-Layer Dispersed Type Foundation

| | |
|---|---|
| Dodecamethyl cyclohexasiloxane | 15 mass % |
| Decamethyl cyclopentasiloxane | Bal. |
| Pulleran 3-tris(trimethylsiloxy)silylpropylcarbamate | 3 |
| Ethanol | 10 |
| Isostearic acid | 0.5 |
| Myristic acid-treated zinc oxide | 0.5 |
| Branched alkyl silicone-coated titanium oxide (*18) | 10 |
| Branched alkyl silicone-coated talc (*1) | 7 |
| Aluminum stearate-coated fine particle titanium oxide | 5 |
| Iron oxide/silicone resin-coated silicone elastomer (Production Example 6) | 5 |
| Spherical anhydrous silicic acid | 2 |
| Magnesium L-ascorbyl 2-phosphate | 0.2 |
| DL-α-tocopherol acetate | 0.1 |
| D-δ-tocopherol | 0.1 |
| 2-ethylhexyl p-methoxycinnimate | 5 |
| Branched alkyl silicone-coated bengara (*16) | q.s. |
| Branched alkyl silicone-coated yellow iron oxide (*15) | q.s. |
| Branched alkyl silicone-coated black iron oxide (*17) | q.s. |
| Fragrance | q.s. |

The cosmetic compositions of Examples 7 to 11 were all excellent in adhesion to the skin and has smooth and moist feelings in use. Further, they had the effects of being high in the cosmetic durability.

The invention claimed is:

1. A powder cosmetic composition comprising, as powder components (a) and (b):
   (a) a branched alkyl silicone-treated powder and
   (b) a composite silicone elastomer powder comprising a dimethicone/vinyl dimethicone crosspolymer, wherein all or part of the composite silicone elastomer powder surface is coated with at least one clay mineral.

2. A powder cosmetic composition as claimed in claim 1, wherein the amount of the component (a) is 3 to 80 mass % and the amount of the component (b) is 1 to 30 mass %.

3. A powder cosmetic composition as claimed in claim 1, wherein the component (a) is a branched alkyl silicone-treated body pigment and/or a branched alkyl silicone-treated coloring material.

4. A powder cosmetic composition as claimed in claim 1, wherein the clay mineral is at least one component selected from the group consisting of sericite, talc, kaolin, mica, and titanium mica.

5. A powder cosmetic composition as claimed in claim 1, wherein the component (b) is a composite silicone elastomer powder having a ratio by mass of coating to silicone elastomer powder of 1:100 to 300:100.

6. A powder cosmetic composition as claimed in claim 1, which is a foundation or eye shadow.

7. A powder cosmetic composition as claimed in claim 1, wherein the powder (a) is treated with a branched alkyl silicone expressed by the general formula (I):

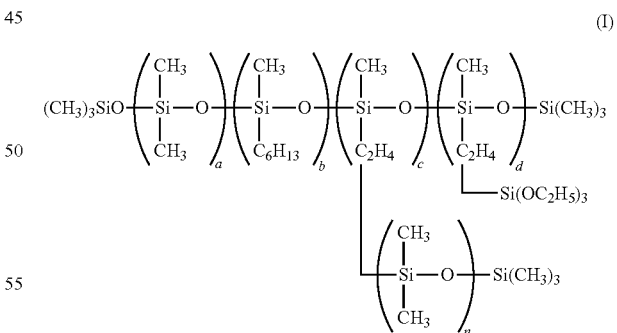

wherein a=5 to 15, b=1 to 5, c=1 to 3, d=1 to 5, and n=3 to 15.

* * * * *